US008399510B2

(12) United States Patent
Wahle et al.

(10) Patent No.: US 8,399,510 B2
(45) Date of Patent: Mar. 19, 2013

(54) METHOD OF ACTIVATING NK CELLS (75) Inventors: Joseph Wahle, St. Louis, MO (US); William Garrow Kerr, Syracuse, NY (US)

(73) Assignee: University of South Florida, Tampa, FL (US)

(*) Notice: Subject to any disclaimer, the term of this patent is extended or adjusted under 35 U.S.C. 154(b) by 356 days.

(21) Appl. No.: 12/577,436

(22) Filed: Oct. 12, 2009

(65) Prior Publication Data

US 2010/0069475 A1     Mar. 18, 2010

Related U.S. Application Data

(63) Continuation of application No. PCT/US2008/059877, filed on Apr. 10, 2008.

(60) Provisional application No. 60/910,950, filed on Apr. 10, 2007, provisional application No. 60/980,612, filed on Oct. 17, 2007.

(51) Int. Cl.
    *A01N 43/16*     (2006.01)
    *A01N 43/00*     (2006.01)
    *A61K 31/35*     (2006.01)
    *A61K 31/33*     (2006.01)

(52) U.S. Cl. .................... 514/454; 514/183
(58) Field of Classification Search .................. 514/454, 514/183

See application file for complete search history.

(56) References Cited

U.S. PATENT DOCUMENTS

| 6,262,044 B1 | 7/2001 | Moller et al. |
| 2003/0095965 A1 | 5/2003 | Van Beneden et al. |
| 2006/0217437 A1 | 9/2006 | Burmester |
| 2006/0241020 A1 | 10/2006 | Huijsduijnen et al. |

OTHER PUBLICATIONS

Vippagunta et al. Advanced Drug Delivery Reviews, vol. 48, 2001, pp. 3-26.*
Daniels, et al., A Natural Killer Cell Receptor Specific for a Major Histocompatibility Complex Class I Molecule, The Journal of Experimental Medicine, 1994, vol. 180, pp. 687-692.
McNerney, et al., 2B4 (CD244)-CD48 Interactions Provide a Novel MHC Class I-Independent System for NK-Cell Self-Tolerance in Mice, Blood, 2005, vol. 106, No. 4, pp. 1337-1340.
Mooney, et al., The Murine NK Receptor 2B4 (CD244) Exhibits Inhibitory Function Independent of Signaling Lymphocytic Activation Molecule-Associated Protein Expression, The Journal of Immunology, 2004, vol. 173, pp. 3953-3961.
Carlyle, et al., Missing Self-Recognition of Ocil/Clr-b by Inhibitory NKR-P1 Natural Killer Cell Receptors, PNAS, 2004, vol. 101, No. 10, pp. 3527-3532.
Iizuka, et al., Genetically Linked C-Type Lectin-Related Ligands for the NKRP1 Family of Natural Killer Cell Receptors, Nature Immunology, 2003, vol. 4, No. 8, pp. 801-807.
Yokoyama, Natural Killer Cell Receptors, Current Opinion in Immunology, 1998, vol. 10, pp. 298-305.
Lanier, Activating and Inhibitory NK Cell Receptors, Mechanisms of Lymphocyte Activation and Immune Regulation VII, 1998, vol. 452, pp. 13-18.
Gasser, et al., The DNA Damage Pathway Regulates Innate Immune System Ligands of the NKG2D Receptor, Nature, 2005, vol. 436, pp. 1186-1190.
Gazit, et al., Lethal Influenza Infection in the Absence of the Natural Killer Cell Receptor Gene Ncr1, Nature Immunology, 2006, vol. 7, No. 5, pp. 517-523.
Mandelboim, et al., Recognition of Haemagglutinins on Virus-Infected Cells by NKp46 Activates Lysis by Human NK Cells, Nature, 2001, vol. 409, pp. 1055-1060.
Lanier, Natural Killer Cell Receptor Signaling, Current Opinion in Immunology, 2003, vol. 15, pp. 308-314.
Kumar, et al., A New Self: MHC-Class-I-Independent Natural-Killer-Cell Self-Tolerance, Nature Reviews, 2005, vol. 5, pp. 363-374.
MacFarlane, et al., Signal Transduction in Natural Killer Cells, CTMI, 2006, vol. 298, pp. 23-57.
Wu, et al., An Activating Immunoreceptor Complex Formed by NKG2D and DAP10, Science, 1999, vol. 285, pp. 730-732.
Sjolin, et al., Pivotal Role of KARAP/DAP12 Adaptor Molecule in the Natural Killer Cell-Mediated Resistance to Murine Cytomegalovirus Infection, The Journal of Experimental Medicine, 2002, vol. 195, No. 7, pp. 825-834.
Billadeau, et al., The Vac-Rac1 Pathway in Cytotoxic Lymphocytes Regulates the Generation of Cell-Mediated Killing, The Journal of Experimental Medicine, 1998, vol. 188, No. 3, pp. 549-559.
Galandrini, et al., Role for the Rac1 Exchange Factor Vav in the Signaling Pathways Leading to NK Cell Cytotoxicity, The Journal of Immunology, 1999, vol. 162, pp. 3148-3152.
Jiang, et al., Syk Regulation of Phosphoinositide 3-Kinase-Dependent NK Cell Function, The Journal of Immunology, 2002, vol. 168, pp. 3155-3164.
Mason, et al., Differential Tyrosine Phoshorylation of Inhibitory Versus Activating Ly-49 Receptor Proteins and Their Recruitment of SHP-1 Phosphatase, The Journal of Immunology, 1997, vol. 159, pp. 4187-4196.
Fry, et al., Phosphotyrosines in the Killer Cell Inhibitory Receptor Motif of NKB1 are Required for Negative Signaling and for Association with Protein Tyrosine Phosphatase 1C, The Journal of Experimental Medicine, 1996, vol. 184, pp. 295-300.
Gupta, et al., Negative Signaling Pathways of the Killer Cell Inhibitory Receptor and FcGammaRllb1 Require Distinct Phosphatases, The Journal of Experimental Medicine, 1997, vol. 186, No. 3, pp. 473-478.
Nakamura, et al., Mouse Ly-49A Interrupts Early Signaling Events in Natural Killer Cell Cytotoxicity and Functionally Associates with the SHP-1 Tyrosine Phosphatase, The Journal of Experimental Medicine, 1997, vol. 185, No. 4, pp. 673-684.

(Continued)

*Primary Examiner* — Samira Jean-Louis
(74) *Attorney, Agent, or Firm* — Nilay J. Choksi; Smith & Hopen, P.A.

(57) ABSTRACT

The present invention provides a method of mediating hypoactivation of NK cells. Methods of the present invention comprise administering to a subject an effective amount of broad acting phosphotase inhibitor, such as sodium orthovanadate, SHP specific inhibitor. In one embodiment, the SHP specific inhibitor is NSC119910.

2 Claims, 6 Drawing Sheets

OTHER PUBLICATIONS

Wang, et al., Influence of SHIP on the NK Repertoire and Allogeneic Bone Marrow Transplantation, Science, 2002, vol. 295, pp. 2094-2097.

Damen, et al., The 145-kDa Protein Induced to Associate with Shc by Multiple Cytokines is an Inositol Tetraphosphate and Phosphatidylinositol 3,4,5-Trisphosphate 5-Phosphatase, Proc. Natl. Acad. Sci. USA, 1996, vol. 93, pp. 1689-1693.

Lioubin, et al., P150Ship, a Signal Transduction Molecule with Inositol Polyphosphate-5-Phosphatase Activity, Genes & Development, 1996, vol. 10, pp. 1084-1095.

Mathew, et al., Cloning and Characterization of the 2B4 Gene Encoding a Molecule Associated with Non-MHC-Restricted Killing Mediated by Activated Natural Killer Cells and T Cells, The Journal of Immunology, 1993, vol. 151, No. 10, pp. 5328-5337.

Veillette, et al., The SLAM Family of Immune-Cell Receptors, Current Opinion in Immunology, 2003, vol. 15, pp. 277-285.

Brown, et al., 2B4, The Natural Killer and T Cell Immunoglobulin Superfamily Surface Protein, is a Ligand for CD48, The Journal of Experimental Medicine, 1998, vol. 188, No. 11, pp. 2083-2090.

Latchman, et al., Cutting Edge: Identification of the 2B4 Molecule as a Counter-Receptor for CD48, The Journal of Immunology, 1998, vol. 161, pp. 5809-5812.

Lee, et al., 2B4 Acts as a Non-Major Histocompatibility Complex Binding Inhibitory Receptor on Mouse Natural Killer Cells, The Journal of Experimental Medicine, 2004, vol. 199, No. 9, pp. 1245-1254.

Veillette, SLAM Family Receptors Regulate Immunity With and Without SAP-Related Adaptors, The Journal of Experimental Medicine, 2004, vol. 199, No. 9, pp. 1175-1178.

Schatzle, et al., Characterization of Inhibitory and Stimulatory Forms of the Murine Natural Killer Cell Receptor 2B4, Proc. Natl. Acad. Sci. USA, 1999, vol. 96, pp. 3870-3875.

Boles, et al., Molecular Characterization of a Novel Human Natural Killer Cell Receptor Homologous to Mouse 2B4, Tissue Antigens, 1999, vol. 54, pp. 27-34.

Nakajima, et al., Activating Interactions in Human NK Cell Recognition: the Role of 2B4-CD48, Eur. J. Immunol., 1999, vol. 29, pp. 1676-1683.

Tangye, et al., Cutting Edge: Human 2B4, an Activating NK Cell Receptor, Recruits the Protein Tyrosine Phosphatase SHP-2 and the Adaptor Signaling Protein SAP, The Journal of Immunology, 1999, vol. 162, pp. 6981-6985.

Vacca, et al., Analysis of Natural Killer Cells Isolated from Human Decidua: Evidence that 2B4 (CD244) Functions as an Inhibitory Receptor and Blocks NK-Cell Function, Blood, 2006, vol. 108, No. 13, pp. 4078-4085.

Eissmann, et al., Molecular Basis for Positive and Negative Signaling by the Natural Killer Cell Receptor 2B4 (CD244), Blood, 2005, vol. 105, No. 12, pp. 4722-4729.

Chen, et al., Molecular Dissection of 2B4 Signaling: Implications for Signal Transduction by SLAM-Related Receptors, Molecular and Cellular Biology, 2004, vol. 24, No. 12, pp. 5144-5156.

Roncagalli, et al., Negative Regulation of Natural Killer Cell Function by EAT-2, a SAP-Related Adaptor, Nature Immunology, 2005, vol. 6, No. 10, pp. 1002-1010.

Tangye, et al., Functional Requirements for Interactions Between CD84 and Src Homology 2 Domain-Containing Proteins and Their Contribution to Human T Cell Activation, The Journal of Immunology, 2003, vol. 171, pp. 2485-2495.

Stepp, et al., Gene Structure of the Murine NK Cell Receptor 2B4: Presence of Two Alternatively Spliced Isoforms with Distinct Cytoplasmic Domains, Eur. J. Immunol., 1999, vol. 29, pp. 2392-2399.

Shlapatska, et al., CD150 Association with Either the SH2-Containing Inositol Phosphatase or the SH2-Containing Protein Tyrosine Phosphatase is Regulated by the Adaptor Protein SH2D1A, The Journal of Immunology, 2001, vol. 166, pp. 5480-5487.

Wahle, et al., Cutting Edge: Dominance by an MHC-Independent Inhibitory Receptor Compromises NK Killing of Complex Targets, The Journal of Immunology, 2006, vol. 176, pp. 7165-7169.

Gordon, Use of Vanadate as Protein-Phosphotyrosine Phosphatase Inhibitor, Methods in Enzymology, 1991, vol. 201, pp. 477-482.

Chen, et al., Discovery of a Novel Shp2 Protein Tyrosine Phosphatase Inhibitor, Molecular Pharmacology, 2006, vol. 70, No. 2, pp. 562-570.

Chuang, et al., Protein Kinase C is Involved in 2B4 (CD244)—Mediated Cytotoxicity and AP-1 Activation in Natural Killer Cells, Immunology, 2003, vol. 109, pp. 432-439.

Thebault, et al., Characterization of TCR-Induced Phosphorylation of PKCTheta in Primary Murine Lymphocytes, Molecular Immunology, 2003, vol. 40, pp. 931-942.

Nedvetzki, et al., Reciprocal Regulation of Natural Killer Cells and Macrophages Associated with Distinct Immune Synapses, Blood, 2007, vol. 109, No. 9, pp. 3776-3785.

Roda-Navarro, et al., Dynamic Redistribution of the Activating 2B4/SAP Complex at the Cytotoxic NK Cell Immune Synapse, The Journal of Immunology, 2004, vol. 173, pp. 3640-3646.

Taniguchi, et al., 2B4 Inhibits NK-Cell Fratricide, Blood, 2007, vol. 110, No. 6, pp. 2020-2023.

Parolini, et al., X-Linked Lymphoproliferative Disease: 2B4 Molecules Displaying Inhibitory Rather Than Activating Function are Responsible for the Inability of Natural Killer Cells to Kill Epstein-Barr Virus-Infected Cells, The Journal of Experimental Medicine, 2000, vol. 192, No. 3, pp. 337-346.

* cited by examiner

METHOD OF ACTIVATING NK CELLS

CROSS REFERENCE TO RELATED APPLICATIONS

This application is a continuation of co-pending International Application, Serial Number PCT/US2008/059877 filed Apr. 10, 2008, which claims priority to U.S. provisional patent application No. 60/910,950 filed Apr. 10, 2007 and U.S. provisional patent application No. 60/980,612 filed Oct. 17, 2007 which is hereby incorporated by reference into this disclosure.

STATEMENT OF GOVERNMENT INTEREST

This invention was made with Government support under Grant No. HL072523 awarded by the National Institutes of Health and a Scholar Award from the Leukemia and Lymphoma Society. The Government has certain rights in the invention.

BACKGROUND OF THE INVENTION

Natural killer (NK) cells are a type of cytotoxic lymphocyte that constitutes a major component of the immune system. NK cells play a major role in the rejection of tumors and cells infected by viruses. The process by which an NK cell recognizes a target cell and delivers a sufficient signal to trigger target lysis is determined by an array of inhibitory and activating receptors on the cell surface. NK discrimination of self from altered self involves inhibitory receptor recognition of MHC-I molecules and non-MHC ligands like CD48 and Clr-1b. NK recognition of infected or damaged cells (altered self) is coordinated through stress induced ligands (e.g., MICA, MICB, Rae1, H60, Mult1) or virally encoded ligands (e.g., m157, hemagluttinin) recognized by various activating receptors, including NKG2D, Ly49H and NKp46/Ncr1.

The process of initial target cell recognition and the recruitment of appropriate downstream signaling molecules to the NK synapse is carefully coordinated in order for the NK cell to effectively kill the target. Although many of the key players in the process are known, the manner in which these disparate steps and pathways are coordinated is less well understood. NK activating receptors, such as NKG2D and Ly49H, upon ligand engagement are able to bind DAP10 or DAP12 molecules that contain an ITAM or YxxM motif. This then allows for the recruitment of various effectors of cell signaling, including the Src and Syk related protein tyrosine kinases that subsequently lead to the activation of more distal effector pathways such as the PI3K and MAP/ERK pathways. Inhibitory receptors that engage self-ligands can oppose activation of these pathways through the recruitment of various SH2 domain-containing phosphatases to their ITIM. These include SHP1 and SHP2, which are responsible for the removal of tyrosine phosphates and the inositol phosphatase SHIP, which is responsible for the removal of the 5' phosphate from PI, P3.

2B4 is a member of the SLAM family of receptors. It functions through the recognition of another SLAM family member, CD48, which is ubiquitously expressed on cells of the hematopoietic system. 2B4 has a complex role in NK cell function and physiology that remains an active area of investigation. Depending on the context 2B4 has been shown to act as both an inhibitory and activating receptor. This is likely due, at least in part, to the ability of 2B4 to differentially recruit various downstream effectors of cell signaling. Under different signaling contexts and in different species 2B4 can recruit SAP, EAT-2, FynT, SHP1, PI3K and SHIP. How the differential recruitment of these signaling entities is controlled is not completely understood. However, which molecules are recruited and thus which signal is propagated following CD48 engagement may be influenced by the ratio of 2B4 isoforms expressed in the NK cell. Two 2B4 isoforms have been identified in mice, short (2B4S) and long (2B4L), that were proposed to have activating and inhibitory signaling capacities, respectively. Although the exact function of these two isoforms remains to be defined, it is feasible that the different intracellular domains within these isoforms could recruit different effectors of cell signaling. 2B4 could also mediate different signaling outcomes through changes in the availability or recruitment of different signaling molecules. For instance, it has been shown that there are diminished levels of the SAP protein in immature human NK cells. The lack of this key activating molecule in the cell appears to lock 2B4 into an inhibitory signaling mode. In other SLAM family members, namely CD150, there is evidence that the presence or absence of SAP can regulate the binding of both SHP1 and SHIP to the immunoreceptor based tyrosine switch motifs (ITSM) of this receptor.

SUMMARY OF INVENTION

It has been previously demonstrated that the NK receptor repertoire is highly disrupted by SHIP-deficiency. This repertoire disruption leads to receptor dominance by 2B4 such that inhibitory signals from 2B4 repress killing of complex targets. Here, the molecular basis for 2B4's dominance of key NK activating receptors is defined for both stress-induced and virally-encoded NK activating ligands.

The present invention provides a method of mediating hyper-activation of NK cells. Methods of the present invention comprise administering to a subject an effective amount of broad acting phosphatase inhibitor, such as sodium orthovanadate, or a SHP specific inhibitor. In one embodiment, the SHP specific inhibitor is a compound of the formula:

or a salt, prodrug, tautomer, hydrate, solvate, or stereoisomer thereof, wherein "a" is an integer from 0 to 4; each $R^1$ is independently hydroxy, alkoxy, halide, alkyl, cyano, nitro, amino, monoalkylamino, dialkylamino, or carboxy; $R^2$ is aryl, cycloalkyl, alkenyl, or alkyl, each of which is optionally substituted; each of $X_1$ and $X^2$ is independently O, S or NR, and $X^3$ is hydrogen, alkoxy, alkyl, hydroxy, halide, amino, monoalkylamino, or dialkylamino.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Definitions

The term "alkenyl" means a linear monovalent hydrocarbon moiety of two to six carbon atoms or a branched monovalent hydrocarbon moiety of three to six carbon atoms, containing at least one double bond, e.g., ethenyl, propenyl, and the like. Alkenyl groups may optionally be substituted with one or more of the substituents, each of which is independently selected from the group: halide, cyano, —C(=O)R (where R is hydrogen, alkyl, haloalkyl, amino, monoalkylamino, dialkylamino, hydroxy, or alkoxy), amino (—NH$_2$), monoalkylamino (—NHR$^a$, where R$^a$ is unsubstituted alkyl), and dialkylamino (—NR$^b$, where each R$^b$ is independently unsubstituted alkyl).

"Alkyl" refers to a saturated linear monovalent hydrocarbon moiety of one to twelve, preferably one to six, carbon atoms or a saturated branched monovalent hydrocarbon moiety of three to twelve, preferably three to six, carbon atoms. Exemplary alkyl group include, but are not limited to, methyl, ethyl, n-propyl, 2 propyl, tert-butyl, pentyl, and the like. Alkyl groups may optionally be substituted with one or more of the substituents, each of which is independently selected from the group: halide (in which case it may be referred to as "haloalkyl"), cyano, —C(=O)R (where R is hydrogen, alkyl, haloalkyl, amino, monoalkylamino, dialkylamino, hydroxy, or alkoxy), amino (—NH$_2$), monoalkylamino (—NHR$^a$, where R$^a$ is unsubstituted alkyl), and dialkylamino (—NR$^b$, where each R$^b$ is independently unsubstituted alkyl).

"Alkylene" refers to a saturated linear saturated divalent hydrocarbon moiety of one to twelve, preferably one to six, carbon atoms or a branched saturated divalent hydrocarbon moiety of three to twelve, preferably three to six, carbon atoms. Exemplary alkylene groups include, but are not limited to, methylene, ethylene, propylene, butylene, pentylene, and the like. Alkylene groups may optionally be substituted with one or more substituents that are disclosed herein in reference to the alkyl group.

"Aryl" refers to a monovalent mono-, bi- or tricyclic aromatic hydrocarbon moiety of 6 to 15 ring atoms which is optionally substituted with one or more substituents within the ring structure. Preferred substituents for the aryl group include alkyl, haloalkyl, halo, nitro, cyano, cycloalkyl, heterocyclyl, —OR (where R is hydrogen, alkyl or haloalkyl, -(alkylene)$_n$-COOR (where n is 0 or 1 and R is hydrogen, alkyl, or haloalkyl), or -(alkylene)$_n$-CONR$^{ab}$ (where n is 0 or 1, and each of R$^a$ and R$^b$ are independently hydrogen, alkyl, cycloalkyl, cycloalkylalkyl, aryl, aralkyl, or R$^a$ and R$^b$ together with the nitrogen atom to which they are attached form a heterocyclyl ring). More specifically the term aryl includes, but is not limited to, phenyl, 1-naphthyl, and 2-naphthyl, each of which may be optionally substituted.

"Cycloalkyl" refers to a non-aromatic, saturated or unsaturated, monovalent mono-, bi-, or tricyclic hydrocarbon moiety of three to twelve ring carbons including bridged ring moieties. The cycloalkyl can be optionally substituted with one or more, preferably one, two, or three, substituents, where each substituent is independently selected from the group consisting of alkyl, haloalkyl, halide, cyano, or C(=O)R (where R is hydrogen, alkyl, haloalkyl, amino, monoalkylamino, dialkylamino, hydroxy, or alkoxy). Exemplary cycloalkyl groups include, but are not limited to, cyclopropyl, cyclohexyl, cyclohexenyl, bicyclo[2.2.1]hept-2-ene, and the like, each of which may be optionally substituted.

"Cycloalkylalkyl" refers to a moiety of the formula —R$^a$R$^b$ where R$^a$ is an alkylene group and R$^b$ is a cycloalkyl group as defined herein.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —CH$_2$Cl, —CF$_2$, —CH$_2$CF$_3$, —CH$_2$CCl$_2$, and the like.

"Heterocyclyl" means a non-aromatic monocyclic moiety of three to eight ring atoms in which one or two ring atoms are heteroatoms selected from N, O, or S(O).sub.n (where n is an integer from 0 to 2), the remaining ring atoms being C, where one or two C atoms can optionally be a carbonyl group. The heterocyclyl ring can be optionally substituted with one or more, preferably one, two, or three, substituents. When two or more substituents are present in a heterocyclyl group, each substituent is independently selected. Preferred substituents for heterocyclyl group include, but are not limited to, alkyl, haloalkyl, heteroalkyl, halo, nitro, cyano, acyl, —C(.dbd.O)R (where R is hydrogen, alkyl, haloalkyl, amino, monoalkylamino, dialkylamino, hydroxy, or alkoxy). More specifically the term heterocyclo includes, but is not limited to, tetrahydropyranyl, piperidino, piperazino, morpholino and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Modulation" refers to a change in the level or magnitude of an activity or process. The change can be either an increase or a decrease. For example, modulation of TGF-.beta. activity includes both increase and decrease in TGF-.beta. activity. Modulation can be assayed by determining any parameter that is indirectly or directly affected by the TGF-.beta. activity. Such parameters include, but are not limited to, cell growth, cell differentiation, and cell morphogenesis.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to a pharmacologically substantially inactive derivative of a parent drug molecule that requires biotransformation, either spontaneous or enzymatic, within the organism to release the active drug. Prodrugs are variations or derivatives of the compounds of the present invention which have groups cleavable under metabolic conditions. Prodrugs become the compounds of the present invention, which are pharmaceutically active in vivo, when they undergo solvolysis under physiological conditions or undergo enzymatic degradation. Prodrugs may require more than one biotransformation steps to release the active drug within the organism. Prodrug forms often offer advantages of solubility, tissue compatibility, or delayed release in the mammalian organism. Prodrugs commonly known in the art include acid derivatives that are well known to one skilled in the art, such as, but not limited to, esters prepared by reaction of the parent acids with a suitable alcohol, or amides prepared by reaction of the parent acid compound with an amine, or basic groups reacted to form an acylated base derivative. Moreover, the prodrugs of the present invention may be combined with other features herein taught to enhance bioavailability. For example, a compound of the present invention having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of a compound of the invention through the carbonyl carbon prodrug sidechain.

"Protecting group" refers to a moiety, except alkyl groups, that when attached to a reactive group in a molecule masks, reduces or prevents that reactivity. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

"A therapeutically effective amount" means the amount of a compound that, when administered to a cell for treating a disease, is sufficient to effect such treatment for the disease. The "therapeutically effective amount" will vary depending on the compound.

When describing a disease (or disorder), the terms "treating" or "treatment" includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

When describing a chemical reaction, the terms "treating", "reacting" and "contacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Compounds of the Present Invention

Some aspects of the present invention are directed to a method of mediating hypo-activation of NK cells in a subject. Without being bound by any theory, it is believed in the SHIP-deficient NK cell there is not only more surface deposition of 2B4, but also significantly more 2B4 protein expressed by SHIP$^{-/-}$ NK cells. It is also demonstrated, that when compared to the WT NK cell, there is a bias in the SHIP$^{-/-}$ NK cell towards the 2B4L isoform. The various signaling molecules that are recruited to 2B4 in SHIP$^{-/-}$ NK cells show a small increase in the PI3K subunits p110 and p85, attributable to increased 2B4 expression. The results disclosed herein also show that there is no demonstrable difference in either SHP2 or EAT-2 recruitment to 2B4. Furthermore, there is approximately 10 to 16 times more SHP1 recruited to 2B4 in SHIP$^{-/-}$ NK cells as compared to WT. The effect of the SHP1 over-recruitment can be reversed by inhibiting SHP1 enzymatic activity using either a broad acting tyrosine phosphatase inhibitor (NaOV) or a more selective SHP inhibitor (NSC119910). These results show that SHIP-deficiency leads not only to 2B4 receptor dominance, but 2B4L bias, as well as altered inhibitory signaling within the SHIP$^{-/-}$ NK cell. A model is disclosed herein incorporating the key differences that exist within 2B4 signaling in the SHIP$^{-/-}$ and WT environment.

Some methods of the present invention comprise a compound of the formula:

or a salt, prodrug, tautomer, hydrate, solvate, or stereoisomer thereof, wherein "a" is an integer from 0 to 4; each $R_1$ is independently hydroxy, alkoxy, halide, alkyl, cyano, nitro, amino, monoalkylamino, dialkylamino, or carboxy; $R_2$ is aryl, cycloalkyl, alkenyl, or alkyl, each of which is optionally substituted; each of $X_1$ and $X_2$ is independently O, S or NR, and $X_3$ is hydrogen, alkoxy, alkyl, hydroxy, halide, amino, monoalkylamino, or dialkylamino.

In one example, a is 1 or 2.

Some of the compounds of the present invention include those where each $R_1$ is independently hydroxy or alkoxy. Preferably, $R_1$ is hydroxy.

Other examples of compounds of the present invention include compounds where $X_1$ is O.

Still other examples of compounds of the present invention include compounds where $X_2$ is O.

Some of the compounds of the present invention include compounds where $X_3$ is hydroxy or alkoxy. Preferably $X_3$ is hydroxy.

Another example of compounds of the present invention include compounds where $R_2$ is substituted aryl (e.g., substituted phenyl), substituted cycloalkyl (e.g., substituted cyclohexyl and substituted bicyclo[2.2.1]hept-2-en-6-yl), substituted alkenyl (e.g., 2-carboxyethenyl), or substituted alkyl (e.g., 2-carboxyethyl). In one particular example, $R_2$ is a penta-substituted phenyl such as 2-carboxy, 3,4,5,6-tetrabromophenyl. In another particular example, $R_2$ is a substituted cyclohexyl, such as 2-carboxy-cyclohexyl, or a substituted bicyclo[2.2.1]hept-2-en-6-yl, such as 5-carboxy-7-methyl bicyclo[2.2.1]hept-2-en-6-yl. Yet another particular example of compounds of the present invention is a substituted ethenyl, for example, 2-carboxyethenyl. Still another particular example of compounds of the present invention includes a substituted alkyl, e.g., 2-carboxyethyl.

Still further, combinations of the exemplary functional groups described herein form other preferred embodiments. In this manner a variety of specific compounds are embodied within the scope of the present invention. A specific compound of the present invention includes:

The compounds of the present invention can exist in unsolvated forms as well as solvated forms, including hydrated forms. In general, the solvated forms, including hydrated forms, are equivalent to unsolvated forms and are intended to be encompassed within the scope of the present invention. In addition to the compounds described above, the compounds of the present invention include all tautomeric forms. Furthermore, the present invention also includes all prodrug forms of the compounds and all stereoisomers whether in a pure chiral form or a racemic mixture or other form of mixture as well as geometric stereoisomers such as (E)- and (Z)-olefins.

The compounds of the present invention are capable of further forming pharmaceutically acceptable acid addition salts. All of these forms are within the scope of the present invention.

Pharmaceutically acceptable acid addition salts of the compounds of the present invention include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate.

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms somewhat in certain physical properties such as solubility in polar solvents, but otherwise the salts are equivalent to their respective free base for purposes of the present invention.

Pharmaceutically acceptable base addition salts can be formed with metal ions or amines, such as alkali and alkaline earth metal ions or organic amines. Examples of metal ions which are used as cations include sodium, potassium, magnesium, calcium, and the like. Examples of suitable amines are N,N'-dibenzylethylenediamine, chloroprocaine, choline, diethanolamine, ethylenediamine, N-methylglucamine, and procaine.

The base addition salts of acidic compounds can be prepared by contacting the free acid form with a sufficient amount of the desired base to produce the salt in the conventional manner. The free acid form can be regenerated by contacting the salt form with an acid and isolating the free acid in the conventional manner. The free acid forms may differ from their respective salt forms somewhat in certain physical properties such as solubility in polar solvents, but otherwise the salts are equivalent to their respective free acid for purposes of the present invention.

The compounds of the present invention can be prepared by a variety of methods which will become apparent to those skilled in the art of organic chemistry. Suitable synthetic methods can readily be formulated given appropriate consideration to protection and deprotection of reactive functional groups by methods standard to the art of organic chemistry. For example, hydroxy groups, in order to prevent unwanted side reactions, sometimes need to be protected (e.g., converted to ethers or esters) during chemical reactions at other sites in the molecule. The hydroxy protecting group is then removed to provide the free hydroxy group. Similarly, amino groups and carboxylic acid groups can be protected (e.g., by derivatization) to protect them against unwanted side reactions.

The starting materials and reagents used in preparing these compounds generally are either available from commercial suppliers, or are prepared by methods known to those skilled in the art. It should be appreciated that various modifications to known synthetic reaction schemes can be made and will be suggested to one skilled in the art having referred to the compounds disclosed herein.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

The examples, below, utilized two phosphatase inhibitors, first a broad acting phosphatase inhibitor NaOV, and second a more specific SHP inhibitor NSC119910. Sodium orthovanadate ($Na_3VO_4$) is an inhibitor of protein tyrosine phosphatases, alkaline phosphatases and a number of ATPases, most likely acting as a phosphate analogue. The $VO_4^{3-}$ ion binds irreversibly to the active sites of most protein tyrosine phosphatases.

Both of these compounds were utilized in an attempt to counteract SHP1 over-recruitment and thereby restore killing by the SHIP$^{-/-}$ NK cells to WT levels. NaOV was able to successfully restore killing by SHIP$^{-/-}$ NK cells of Rae1$^+$ cells to WT levels. Interestingly the killing of RMA parental cells by SHIP$^{-/-}$ NK cells was also significantly increased. The demonstrate this increase in SHIP$^{-/-}$ killing results from the under representation of other inhibitory receptors, for MHC-I ligands, in SHIP$^{-/-}$ NK cells, that would prevent WT killing of MHC-I$^+$ targets that lack activating ligands. Therefore, when inhibitory dominance of 2B4 is released by phosphatase blockade this presumably enables supernormal killing of MHC-I$^+$ targets that lack activating ligands. Although it is possible that the use of the broad acting NaOV is having an effect on other phosphatases in the SHIP$^{-/-}$ NK cell it is unlikely due to the fact that 2B4 is dominant inhibitory receptor in the SHIP$^{-/-}$ NK cell. Most importantly the results show a consistent increase in SHIP$^{-/-}$ cytotoxicity in the presence of NaOV reconfirming the ability of phosphatase blockade to increase cytotoxicity of the hypo-responsive SHIP$^{-/-}$ NK cell against BaF3 and m157$^+$ cells. Importantly, the more specific NSC119910 was tested, but the same increase of killing of m157$^+$ cells by WT LAK cells was not seen, indicating that the increase with NaOV is due to non-SHP1 related effects.

The use of the more specific SHP inhibitor NSC119910 confirms initial findings that the blockade of SHP1 mediated inhibition restores killing by SHIP$^{-/-}$ NK cells. A very dramatic and significant increase in killing by the SHIP$^{-/-}$ cells was seen during the killing of RMA and Rae1$^+$ cells. Although an increase in the killing of RMA cells by WT NK cells was observed in the presence of NSC119910, possibly due to blocking of 2B4 independent inhibitory signals. It is likely that in the WT NK environment the enhancement we see for killing of syngeneic parental cells that lack the activating ligand is due to inhibition of SHP1 and/or SHP2 recruited to MHC receptors, rather than 2B4. In the WT environment it may be possible to have 2B4 independent mechanisms at work, where in the SHIP$^{-/-}$ NK cell it is 2B4 dependent mechanisms rendering the cells hypo-responsive.

a. EXAMPLES

SHIP$^{-/-}$ mice were created in the lab and maintained by intercrossing SHIP$^{+/-}$ mice (F10 to the C57BL6/J background). All Western blot and tumor cytolysis studies were performed with SHIP$^{-/-}$ and WT littermates between 6-9 weeks of age. All studies were performed in accordance with the guidelines and approval of the Institutional Animal Certification and Use Committee (IACUC) at the University of South Florida.

LAK Cultures and Cytolysis Assays

NK cells were magnetically enriched from whole splenocytes using the Miltenyi mouse NK cell enrichment kit and an Automac (Miltenyi) per the manufacturer's instructions. Magnetically enriched cells were plated at 2×10$^6$ cells/mL in the presence of 2000 units/mL human rIL-2 (Proleukin). Non-adherent cells were removed on day 2 and media replaced as necessary. On day 7 a standard 4 hour chromium release assay was performed. Briefly, target cells were loaded with 100 µCi of 51Cr per 1×10$^6$ cells for 60 minutes at 37° C. The target and lymphokine activate killer (LAK) 3 cells were then incubated together at 37° C. for 4 hours in the presence of inhibitors or media alone. Supernatants were collected and measured for radioactivity on a gamma counter (Perkin Elmer Wizard1470).

Inhibitors

All experiments using sodium orthovanadate (NaOV) were performed with 100 µM activated NaOV. NaOV was activated by adjusting the pH of a 200 mM stock to pH 10.0 by the addition NaOH or HCl followed by boiling until the solution becomes colorless and then cooling to room temperature. This process is then repeated until the pH of the NaOV stabilizes at 10.0 (44). NaOV was added to the wells of the killing assay with the LAK cells 15 to 30 min prior to adding target cells at room temperature. NSC119910 was obtained from the Drug Synthesis and Chemistry Branch, Developmental Therapeutics Program, Division of Cancer Treatment and Diagnosis, NCI. The structure of NSC119910 was confirmed by proton NMR using a Varian Mercury-Plus, Oxford AS400 spectrometer. The 1H NMR spectrum was recorded at 400 MHz using DMSO-d6 as solvent and tetramethylsilane (TMS) as an internal standard. Chemical shift values are reported in parts per million (δ). The compound shows characteristic signals as follows: δ 12.643 (s, 1H, —OH, disappeared on D$_2$O shake), 12.432 (s, 1H, —OH, disappeared on D$_2$O shake), 10.103 (br s, 1H, disappeared on D$_2$O shake), 7.486 (d, J=9.2 Hz, 1H, Ar), 7.411 (d, J=9.2 Hz, 1H, Ar), 6.438 (d, J=8.8 Hz, 1H, Ar), 6.403 (d, J=9.2 Hz, 1H, Ar), 2.024-0.796 (m, cyclohexyl moiety). NSC119910 has a cell free, in vitro $IC_{50}$ of 2.7 µM using purified SHP1. 25 times this IC50 was established as the effective dose for NK cell based assays. NSC119910 was added immediately before the addition of target cells on ice. Both compounds were tested at their working concentration for the ability to kill and/or lyse the target cells without LAK cells being present. In all instances, no cell death or chromium release above background was observed in the presence of the inhibitors.

Western Blots and Immunoprecipitates

For Western blots and immunopreciptitations (IPs) whole cell lysates were made from sorted $SHIP^{-/-}$ or WT NK cells or LAK cells as indicated. For LAK cells 7 day LAK cultures were prepared as described above, the purity of the LAK cells at the end of the 7 days was 90-95%. For freshly isolated non-stimulated NK cells spleens were removed form $SHIP^{-/-}$ and WT littermates. Whole splenocytes were prepared from the spleen, red blood cell lysed and Fc blocked with and anti CD16/32 (Becton Dickson). The cells were stained with $NK1.1^+$, FITC, TCRβ PE and DAPI. NK cells were then sorted on the basis of $NK1.1^+$, $TCRβ^-$ and $DAPI^-$ on a FACS Aria (Becton Dickson). Cells were lysed for 30 minutes on ice in a modified TNE buffer consisting of 50 mM Tris-HCl, 1% NP-40, 150 mM NaCl, 1 mM EDTA, 1 mM PMSF, 1 mM NaOV, 1 mM NaF, and protease inhibitors. For Western blots equal cell equivalents for $SHIP^{-/-}$ and WT lysates were resolved on a 4-12% Bis-Tris gel (Invitrogen) and transferred to an ECL membrane (Amersham). Blots were blocked with 5% NFM-PBS-T. Primary antibodies were used at varying concentrations; p110 (Cell Signaling, 1:1000), p85 (Cell signaling, 1:1000), Eat-2 (a kind gift of Andre Veillette, 0.5 µg/mL), SHP1 (BD Transduction Laboratories, 1:500), SHP2 (1:1000 Cell Signaling), 2B4 (R&D, 0.2 µg/mL). The appropriate anti-IgG HRP secondary was used and resolved with the Super Signal HRP detection system (Pierce). Quantification was performed using Imagequant software (GE Healthcare). The Integrated Density Value $(IDV)^3$ is calculated by area×(mean Density−background). To assure that areas of differing size did not skew quantitation bands were delineated by boxes of the same area between samples that would be directly compared (i.e.: SHP1 between $SHIP^{-/-}$ and WT). For fluorochrome tagged secondary antibodies the appropriate anti-IgG conjugated to an Alexafluor 488 or 680 (Invitrogen) was utilized. For immunoprecipitates $(IP)^3$ cells were lysed in modified TNE lysis buffer consisting of 50 mM Tris-HCl, 1% NP-40, 150 mM NaCl, 1 mM EDTA, 1 mM PMSF, 1 mM NaOV, 1 mM NaF, and protease inhibitors. Lysates were precleared with protein G sepharose beads at 4° C. for 60 minutes. Cleared lysates were then incubated with an anti-2B4 antibody (BD) for 60 minutes at 4° C. while rocking. Protein G beads (eBioscience) were then added to the lysates for 60 minutes at 4° C. while rocking, after which the protein G beads were washed 6 times with cold TNE buffer. IPs were then resolved by SDS-PAGE and blotted as described.

PTP Inhibition Assay

PTP activity was measured using the fluorogenic 6,8-difluoro-4-methylumbelliferyl phosphate (DiFMUP; Invitrogen, Carlsbad, Calif.) as the substrate. Each reaction contained 25 mM HEPES, 50 mM NaCl, 0.05% Triton, 1 mM dithiothreitol, 20 µM DiFMUP, 10 nM Microcystin LR, 20 nM GST-PTP, and 10 µl of test compound or dimethyl sulfoxide (solvent) in a total reaction volume of 100 µl in black 96-well plates. Reaction was initiated by addition of DiFMUP, and the incubation time was 30 min at room temperature. DiFMUP fluorescence signal was measured at an excitation of 355 nm and an emission of 460 nm with a plate reader (Victor2 1420; PerkinElmer Wallac, Gaithersburg, Md.). $IC_{50}$ was defined as the concentration of an inhibitor that caused a 50% decrease in the PTP activity. For $IC_{50}$ determination, eight concentrations of NSC119910 at one-third dilution (~0.5 log) were tested. The ranges of NSC119910 concentrations used in each PTP assay were determined from preliminary trials. Each experiment was performed either in triplicate or duplicate, and $IC_{50}$ data were derived from at least two independent experiments. The curve-fitting program Prism 4 (GraphPad Software, San Diego, Calif.) was used to calculate $IC_{50}$ values.

Statistical Analysis

Statistical analysis was done using Graphpad Prism. The statistical test that was utilized was a Students two-tailed T-test. N=3 except where a greater N is indicated. Results were considered significant with a $p<0.05$.

Example I

2B4 and SHP Expression in Ship-Deficient NK Cells

Figure 1:
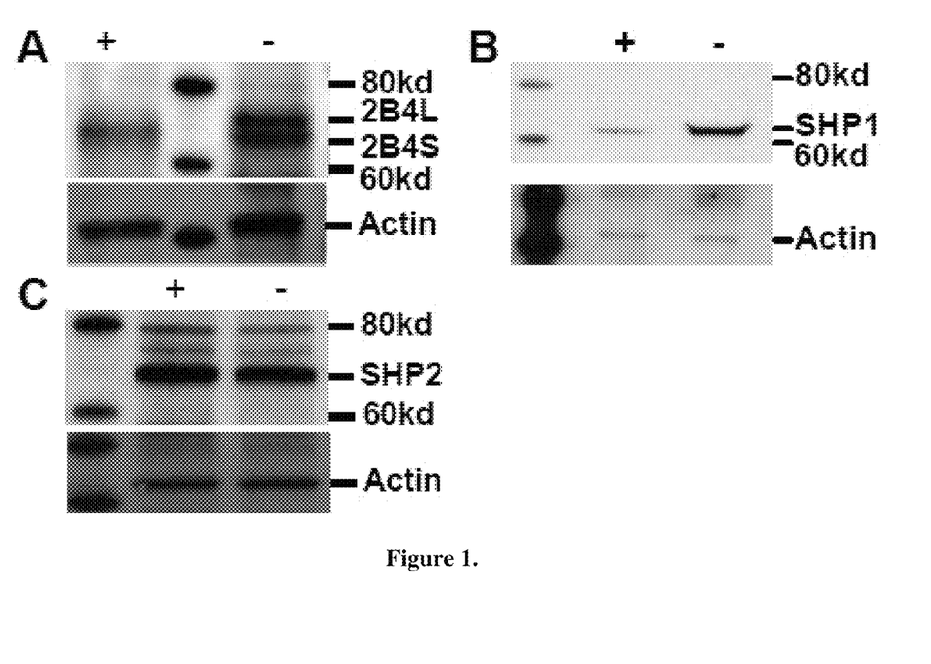
FIG. 1 is a series of protein blots showing expression of signaling molecules (A) 2B4, (B) SHP1, and (C) SHP2 in NK WCL.

2B4 levels are increased on the surface of $SHIP^{-/-}$ NK cells. To determine if this increase is due to increased expression of 2B4, rather than increased surface deposition, NK1.1+ TcRb— NK cells were sorted from spleens of SHIP-/- (−) and WT (+) mice. Whole cell lysates were prepared from sorted $SHIP^{-/-}$ and WT NK cells, that were non-stimulated, for the presence of 2B4 (FIG. 1A) and blotted. The analysis revealed, consistent with previous FACS analysis, that steady state levels of 2B4 are increased in $SHIP^{-/-}$ NK cells. The ratio of 2B4S to 2B4L was also found skewed towards the long isoform (2B4L) in the SHIP-/- NK cell relative to WT NK cells. In addition to 2B4, whole cell lysates $(WCL)^3$ were blotted for SHP1 (FIG. 1B) and SHP2 (FIG. 1C). This revealed that like 2B4, SHP1 is over-expressed in $SHIP^{-/-}$ NK cells as compared to WT. In contrast SHP2 levels are consistently comparable between $SHIP^{-/-}$ and WT NK cells. These Western blots are representative of three independent experiments.

Example II

Increased Recruitment of SHP1 to 2B4 in SHIP-Deficient NK Cells

Figure 2:
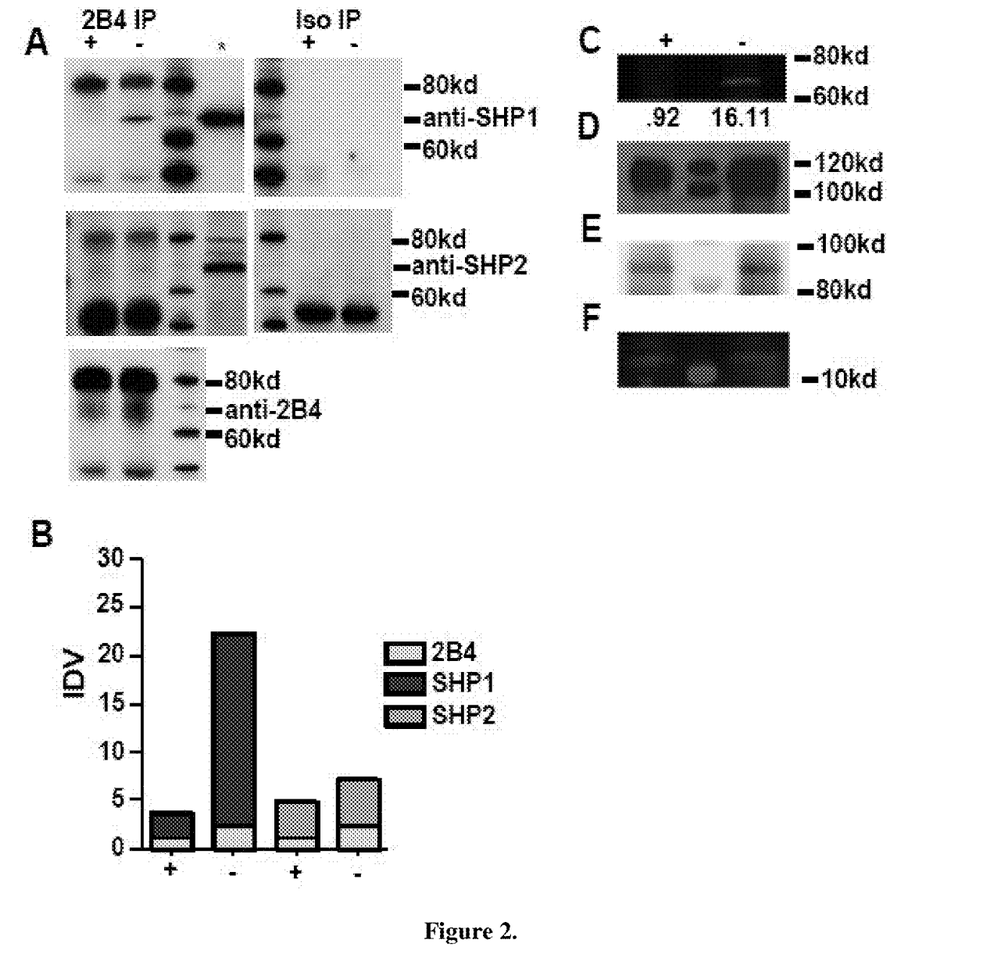
FIG. 2 is a series of protein blots and graph showing the recruitment of signaling molecules to 2B4 in resting NK cells using immunoprecipitation. The IP were probed for (A) 2B4. Protein levels of SHP 1 and SHP 2 were quantified and graphed (B), showing SHP1 and SHP2 levels in comparison to 2B4. 2B4 IPs were probed for (C) SHP1, (D) p110 subunit of PI-3-Kinase, (E) p85 subunit of PI-3-Kinase, of (F) EAT-2.

Due to the over-expression of 2B4, the bias towards the 2B4L isoform and SHP1 over-expression the inventors deduced a qualitative change in signals emanating from 2B4 in $SHIP^{-/-}$ NK cells. To examine this possibility, 2B4 IPs were prepared from sorted $SHIP^{-/-}$ and WT NK cells that were non-stimulated (FIG. 2). NK1.1+TcRb—NK cells were sorted from spleens of SHIP-/- (−) and WT (+) mice. WCL were then prepared from the purified NK cells and 2B4 IPs prepared. 1,000,000 cell equivalents were used for all IPs. Given the increase of SHP1 in $SHIP^{-/-}$ NK cells, the inventors explored the recruitment of it as well as SHP2 to 2B4. 2B4 and its isotype control were IP in parallel. The IPs were then blotted for SHP1 and SHP2. 2B4 was blotted in the IPs to determine the total amount of receptor that was precipitated in order to normalize the samples (FIG. 2A). The results show a substantial increase in the recruitment of SHP1 to 2B4 in the $SHIP^{-/-}$ NK cell as compared to WT NK cells. However, there is no change in SHP2 recruitment to 2B4 between $SHIP^{-/-}$ and WT NK cells. These blots were subsequently stripped and re-probed for 2B4. The amount of SHP1, SHP2 and 2B4 present in these IPs was quantified using Imagequant software, allowing a comparison of the relative amount of each of these proteins present in the IPs. The results show that although there is an increase in 2B4 in the null IP there is a much greater increase in SHP1 (FIG. 2B). Through this comparison, an approximately 2-fold increase in 2B4 is observed in the SHIP$^{-/-}$ 2B4 IPs compared to WT. This 2-fold greater amount of 2B4 in the SHIP$^{-/-}$ NK cell was expected, since, as previously shown, there is approximately 2-fold increase in the amount of 2B4 on the surface of SHIP$^{-/-}$ NK cells as measured by flow cytometry. Therefore if equal cell equivalents were loaded one would expect ~2-fold more 2B4 in the IPs of SHIP$^{-/-}$ NK cells as compared to WT IPs. It is also shown that in the SHIP$^{-/-}$ IPs have at least a 10-fold increase in SHP1 recruitment, so although there is more 2B4 in SHIP$^{-/-}$ IPs there is dramatically more SHP1. The same analysis was performed of SHP1 recruitment to 2B4 using a chemiluminescent secondary and a Licor Odyssey imager. This allowed quantitation of the amount of SHP1 recruited to 2B4. The results reconfirm the SHP1 finding showing that there is approximately 16 times more SHP1 recruited to 2B4 in the SHIP−/− NK compared to the WT.

Given the key role of SHIP in opposing PI3K signaling, PI3K was blotted for subunits p110 and p85. SHP1 was probed for in 2B4 IPs using a fluorochrome tagged secondary and developed on a Licor Odyssey imager allowing the intensity of the SHP1 bands to be quantitated (FIG. 2C), the resulting values shown below each band in arbitrary fluorescence units (FU). The IPs were then probed for p110 subunit of PI-3-Kinase WB on 2B4 IPs (FIG. 2D), and p85 subunit of PI-3-Kinase WB on 2B4 IPs (FIG. 2E). In both instances a small but consistent increase in the association of 2B4 with both PI3K subunits was seen in SHIP$^{-/-}$ NK cells. This change likely reflects increased 2B4 expression in SHIP-deficient NK cells, rather than preferential recruitment of these PI3K subunits. EAT-2 has been proposed to be a key mediator of the 2B4 inhibitory pathway, and therefore 2B4 IPs were also blotted for EAT-2 no appreciable difference was observed (FIG. 2F). These IP and Western blots are representative of three independent experiments.

Figure 3:
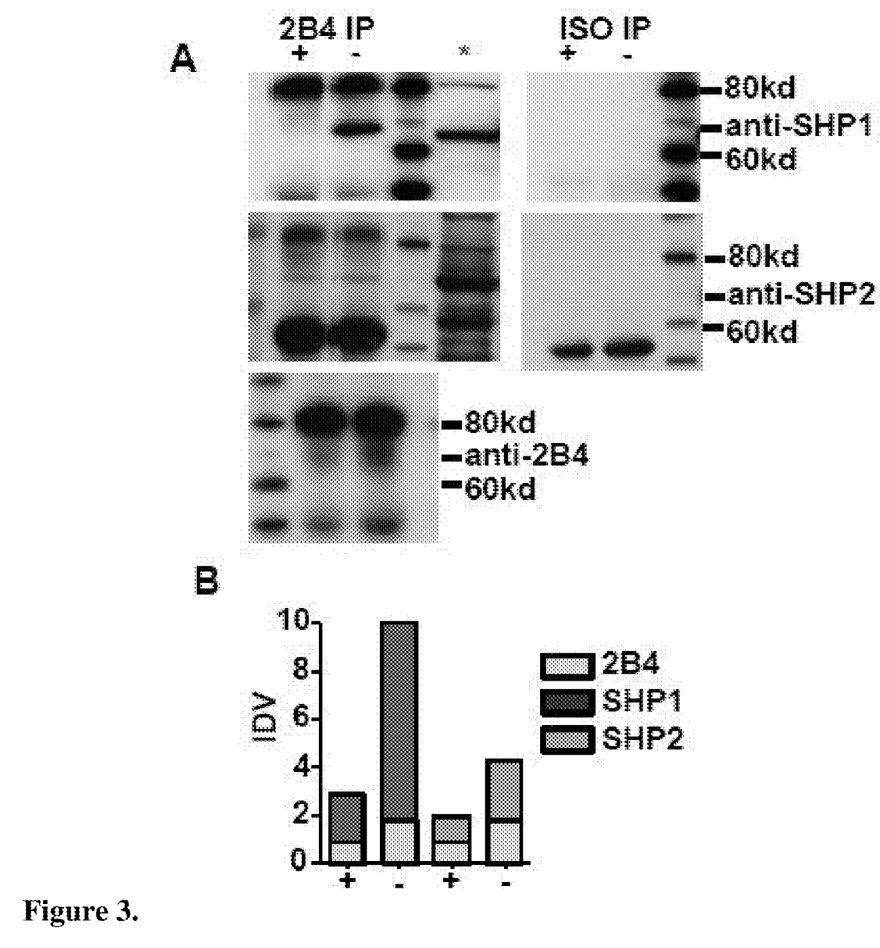
FIG. 3 is a (A) protein blot of SHP1, SHP2 and 2B4, and quantified. The data was then graphed (B) showing the recruitment of signaling molecules to 2B4 in activated NK cells using immunoprecipitation.

Given that the functional assays of 2B4's impact on NK cytolytic function are performed with LAK cells (FIGS. 4, 5), SHP1 and SHP2 were also examined for recruitment to 2B4 receptor complexes in SHIP$^{-/-}$ and WT LAK cells. 2B4 and its isotype control were immunoprecipitated in parallel from WCL of SHIP−/− (−) and WT (+) LAK cells, using 1,000,000 cell equivalents were used for all IPs. The IPs were resolved by SDS-PAGE and then Western blotted. SHP1 and SHP2 were probed, with 2B4 blotted in the 2B4 IPs to normalize the amount of receptor present in the IP. (FIG. 3A) As was observed with freshly isolated NK cells there is a dramatic, and surprising, increase in the recruitment of SHP1 to 2B4 in activated SHIP$^{-/-}$ NK cells compared to WT where SHP2 remains equal in the same cells (FIG. 3A). SHP1, SHP2 and 2B4 levels were then quantified using Imagequant software and compared in a bar graph, showing that SHP1 is dramatically over-recruited to 2B4 in the SHIP−/− LAK cells compared to the WT (FIG. 3B). These IP and Western blots represent three independent experiments The amount of SHP1, SHP2 and 2B4 present in the 2B4 IPs was quantitated. This finding agreed with the finding in resting NK cells that even though there is a 2-fold increase in 2B4 expression in the SHIP$^{-/-}$ NK cell the increased recruitment of SHP1 is much greater. Taken together, the analysis of both resting and activated NK cells suggests that 2B4 dominance of activating receptors and the hypo-responsiveness of SHIP$^{-/-}$ NK cells could be due to an inappropriate degree of SHP1 recruitment to 2B4 receptor complexes.

Example III

Figure 4:
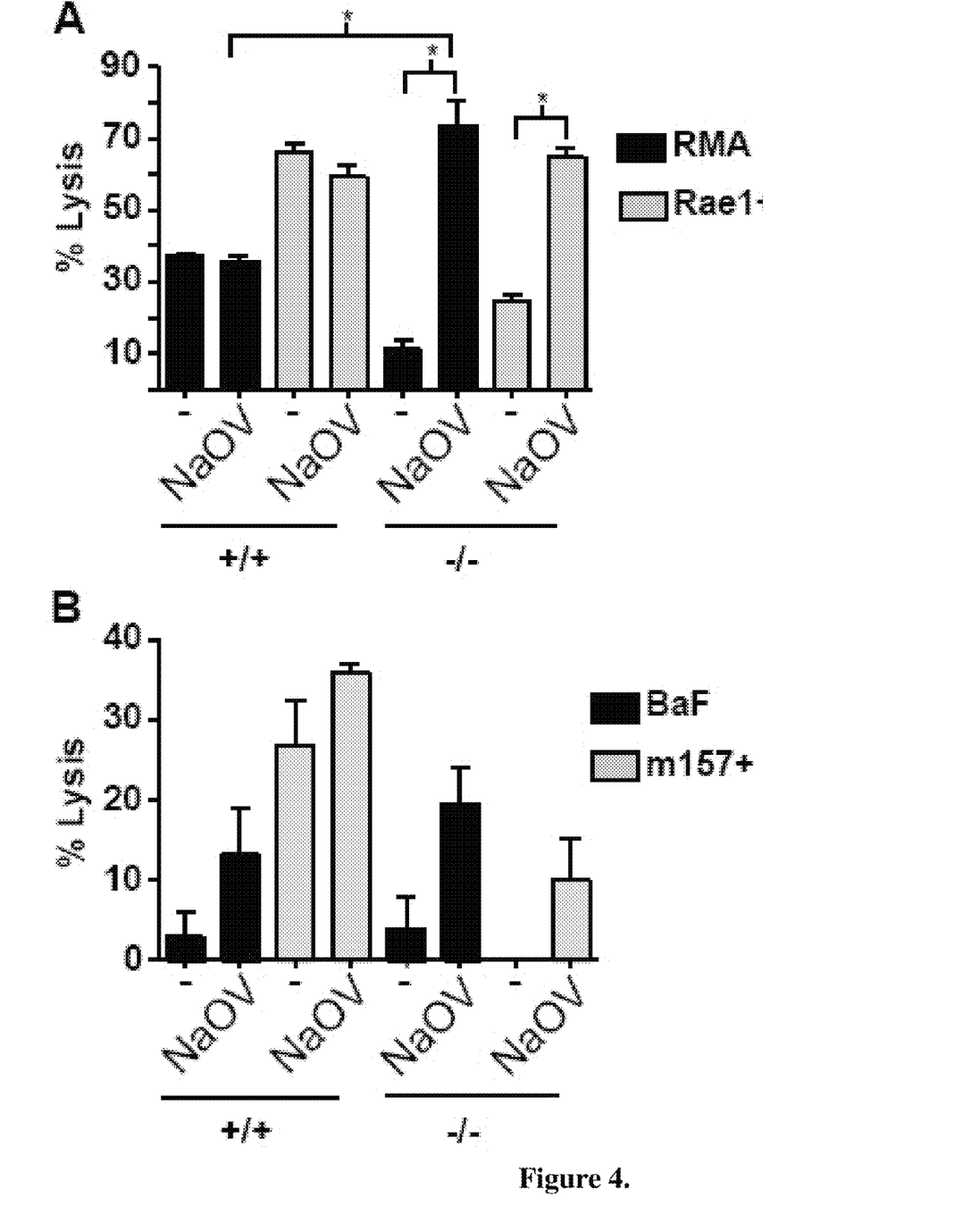
FIG. 4 shows the restoration of cytotoxicity after NaOV treatment in (A) RMA or Rae1+ RMA transfectants or (B) BaF or M157+ BAF cells.

Broad Inhibition of Tyrosine Phosphatase Activity Restores SHIP$^{-/-}$ NK Cytolytic Function Given the inappropriate degree of SHP1 recruitment to 2B4 in SHIP$^{-/-}$ NK cells, the possibility of using chemical inhibitors to block its tyrosine phosphatase activity was explored to determine if this could restore killing of complex targets by SHIP-deficient NK cells. Standard four-hour 51Cr release assays were performed with SHIP$^{-/-}$ (−/−) or WT (+/+) LAK cells, with a ratio of 30:1 and 3000 target cells for all conditions. NaOV (100 μM) was used first, a broadly acting tyrosine phosphatase inhibitor to counteract the effects of the SHP1 over-recruitment to 2B4, with a medium-only negative control. The addition of 100 μM sodium orthovanadate to SHIP$^{-/-}$ NK cytolysis assays was found to restore cellular ability to mediate efficient killing (FIG. 4A). Importantly, increased killing by WT LAK cells was not seen against either RMA or RMA-Rae1$^+$ transfectant-targets (FIG. 4A) following the addition of NaOV. However, it was also observed that NaOV treatment increased the capacity of SHIP$^{-/-}$ NK cells to kill RMA parental cells that do not express the NKG2D ligand, Rae1. In fact, SHIP-deficient NK cytolysis of RMA parental targets exceeds that of WT LAK cells. This supernormal killing has been consistently observed against RMA targets in three separate studies with NaOV-treated SHIP$^{-/-}$ LAK cells. This finding indicates phosphatase inhibition can restore the ability of SHIP$^{-/-}$ NK cells to kill complex targets via NKG2D, while also expanding the capacity of SHIP-deficient NK cells to kill tumor cells in the absence of ligands for NKG2D.

The ability of NaOV to increase cytotoxicity with BaF3 and m157$^+$ BaF3 targets (FIG. 4B) was also tested. It was observed that NaOV is able to increase the capacity of SHIP$^{-/-}$ NK cells to kill both the parental BaF3 cells as well as the activating ligand positive m157$^+$ BaF3 cells. Although these differences are not as dramatic as is seen in NKG2D killing, such increased killing is consistently observed with both BaF3 parental and m157$^+$ targets. RMA and BaF3 cell lines were examined for the expression of the 2B4 ligand CD48 and found to both have CD48 ubiquitously expressed (data not shown). Taken together with results demonstrating 2B4 dominates NKG2D and Ly49H in SHIP-deficient NK cells, the ability of NaOV to restore killing by SHIP$^{-/-}$ NK cells against multiple targets indicates increased tyrosine phosphatase activity is locking the SHIP$^{-/-}$ NK cell into a hypo-responsive state.

Example IV

Inhibition of SHP1 Activity Restores SHIP$^{-/-}$ NK Cytolytic Function

Figure 5:
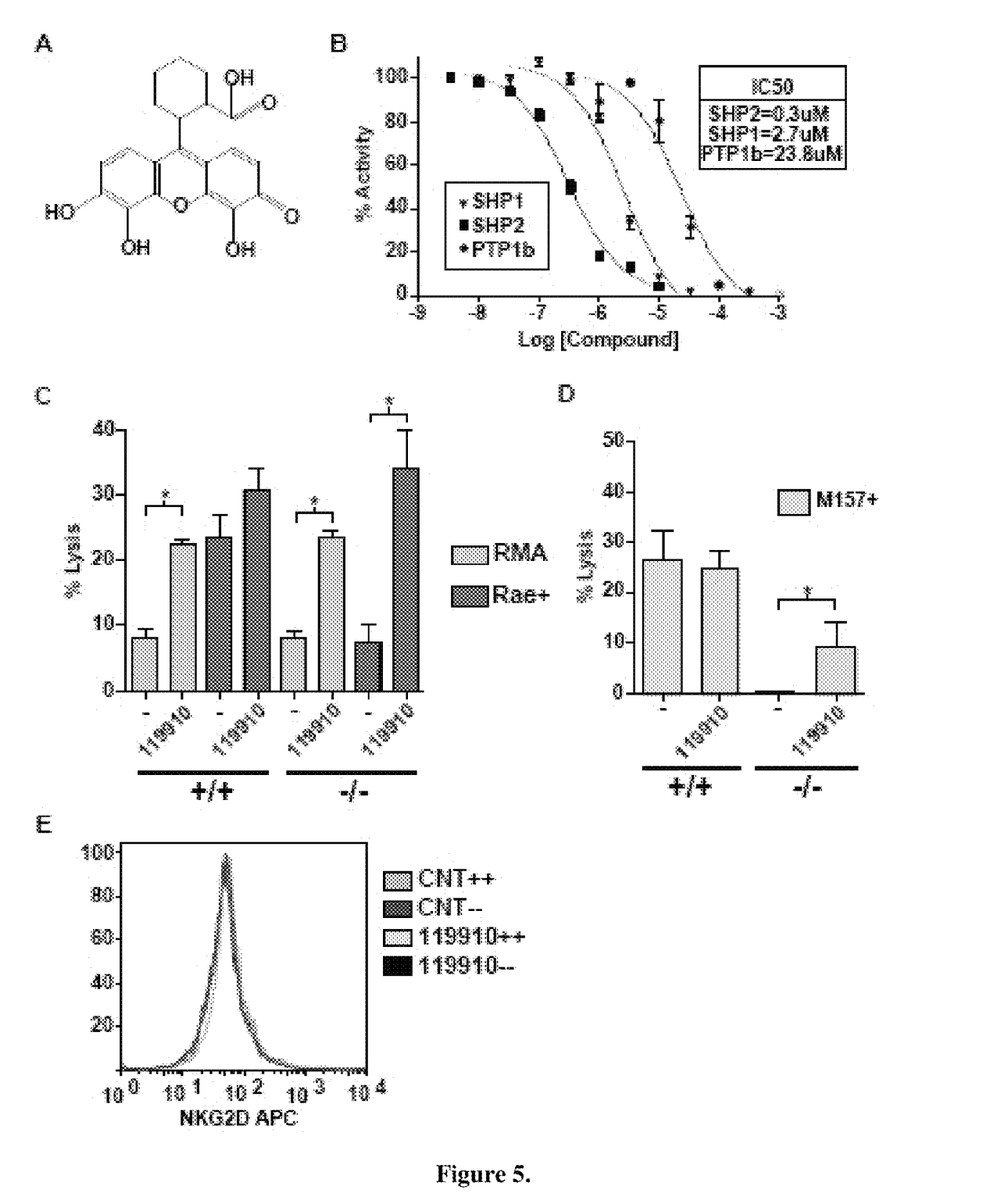
FIG. 5 shows the restoration of cytotoxicity through SHP1/2 inhibitor, NSC119910 (A) in SHIP−/− NK cells, by testing the phosphatase activity (B) of SHP1, SHP2 and PTP1b. C-D) 51Cr release assays were performed with SHIP−/− (−/−) or WT (+/+) LAK cells in the presence of 67.32 μM NCI119910 or media alone (−), using (C) Rae1+ RMA or (D) M157+ BaF3 as targets. E) SHIP$^{-/-}$ or WT cells were incubated with NSC119910 or media alone.

To further test the hypothesis that inappropriate recruitment of SHP1 to 2B4 is locking SHIP$^{-/-}$ NK cells into a hypo-responsive state, several novel low MW compounds that have the ability to inhibit the phosphatase activity of SHP1 at μM levels were tested. These compounds were identified during a screen for SHP2 inhibitors. Six compounds were screened with predicted μM activity against SHP1 and 2. Of these 6 compounds one was identified, NSC119910 (FIG. 5A), which was particularly effective in restoring the cytolytic capacity of SHIP$^{-/-}$ NK cells. The structure of this molecule was confirmed by proton NMR (see Materials and Methods). The selectivity and ability to inhibit the phosphatase activity of SHP1 and 2 of NSC119910 was tested in vitro against SHP1, SHP2 and PTP1b (FIG. 5B). These experiments demonstrate that NSC119910 is approximately 10-fold more selective to SHP1 and approximately 100-fold more selective to SHP2 than a very closely related tyrosine phosphatase PTP1b.

Next, the ability of NSC119910 to restore killing in the SHIP$^{-/-}$ NK cell was tested. The effective in vitro dose at which NSC119910 was able to restore SHIP$^{-/-}$ cytotoxicity was determined in a dose titration experiment. Through this, 67.32 µM was identified as the effective dose (data not shown). This concentration of 67.32 µM of NSC119910 was used for all subsequent standard 4-hour 51Cr release assays, performed with SHIP$^{-/-}$ ($^{-/-}$) or WT ($^{+/+}$) LAK cells and using a ratio of 30:1 and 3000 target cells in the presence of 67.32 µM NCI119910 or media alone (−). The addition of NSC119910 significantly restored killing of Rae1+ RMA as well as parental RMA targets by SHIP$^{-/-}$ NK cells, while it had no effect on the cytolytic activity of WT NK cells against Rae1$^+$ targets (FIG. 5C). The experiments were repeated, using M157+ BaF3 transfectants were used as targets (FIG. 5D). SHIP$^{-/-}$ ($^{--}$) or WT ($^{++}$) cells were incubated with 67.32 µM NSC119910 (119910) or media alone (CNT) for 4 hours. The cells were then stained for NK1.1, TCR-β and NKG2D and analyzed for NKG2D expression. The addition of NSC119910 to LAK cells had no effect on the expression levels of NKG2D (FIG. 5E). The experiments were also performed with m157$^+$ BaF3 targets. As shown in FIG. 5 the addition of NSC119910 also increased SHIP$^{-/-}$ NK killing of m157$^+$ targets. Although the increase is not as dramatic as observed with NKG2D mediated cytolysis, this increase has been observed consistently in multiple cytolysis assays with the m157$^+$ BaF3 targets. These tyrosine phosphatase inhibition studies when paired with the biochemical determination of inappropriate SHP1 recruitment to 2B4 in SHIP$^{-/-}$ NK cells provides a mechanistic rationale for the hypo-responsiveness of SHIP$^{-/-}$ NK cells.

Figure 6:
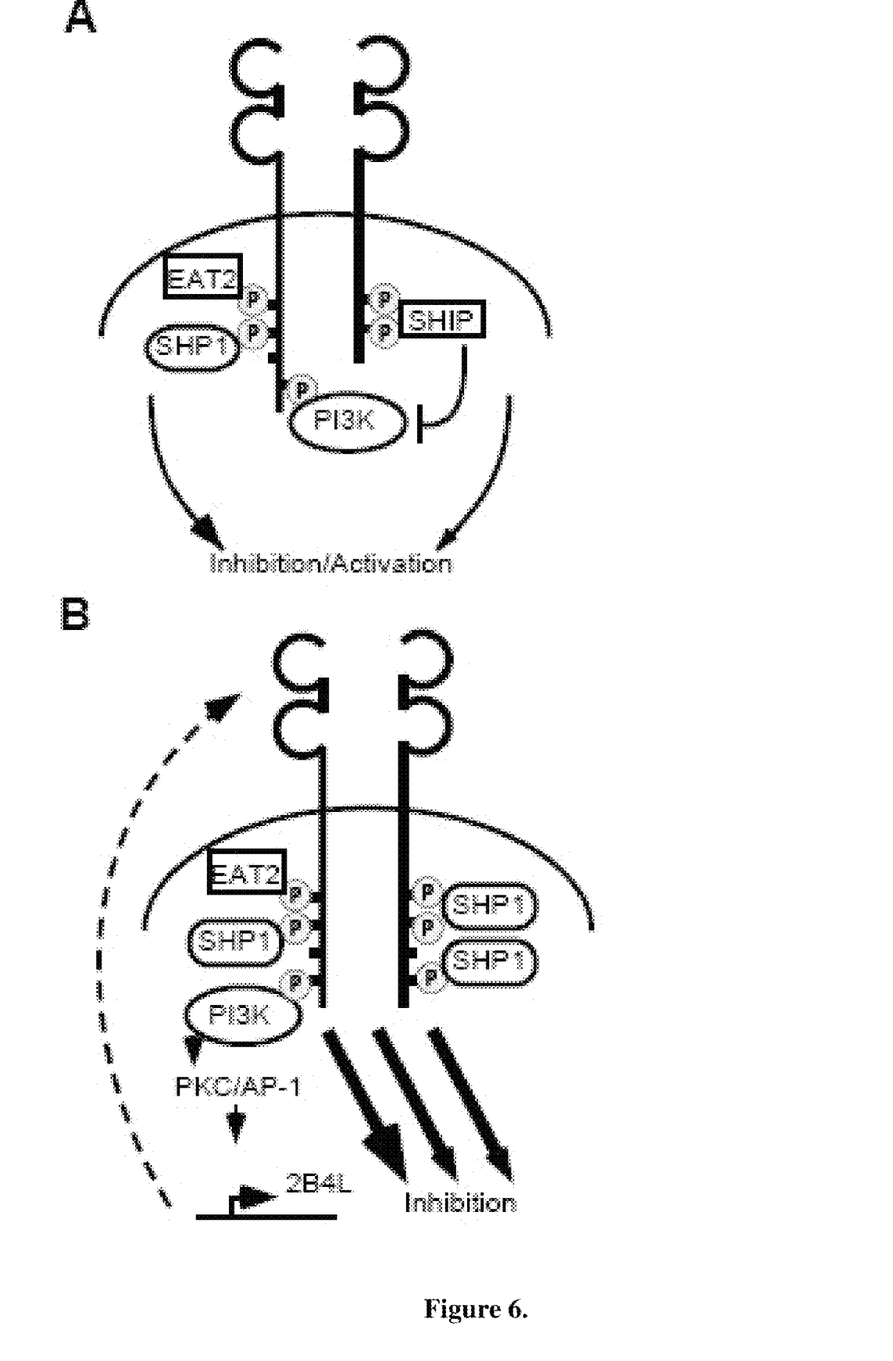
FIG. 6 is a model figure of 2B4 signaling in a (A) WT NK cell or (B) SHIP$^{-/-}$ NK cell.

The inventors have shown that SHIP-deficiency leads to an NK receptor repertoire disruption such that 2B4 acts as a dominant inhibitory receptor (see Wahle, J. A., K. H. Paraiso, A. L. Costello, E. L. Goll, C. L. Sentman, and W. G. Kerr. 2006. Cutting edge: dominance by an MHC-independent inhibitory receptor compromises NK killing of complex targets. *J Immunol* 176:7165-7169; which is incorporated herein by reference). These findings are extended here to identify a molecular mechanism responsible for 2B4 receptor dominance in SHIP$^{-/-}$ NK cells. It has been previously shown that there is significant over representation of 2B4 on the surface of SHIP$^{-/-}$ NK cells. This observation was extended, demonstrating that in the SHIP-deficient NK cell there is not only more surface deposition of 2B4, but also significantly more 2B4 protein expressed by SHIP$^{-/-}$ NK cells. It was also determined that when compared to the WT NK cell, there is a bias in the SHIP$^{-/-}$ NK cell towards the 2B4L isoform. The various signaling molecules that are recruited to 2B4 in SHIP$^{-/-}$ NK cells was examined, showing a small increase in the PI3K subunits p110 and p85, most likely attributable to increased 2B4 expression. The inventors also identified that there is no demonstrable difference in either SHP2 or EAT-2 recruitment to 2B4. Furthermore the inventors identified that there is approximately 10 to 16 times more SHP1 recruited to 2B4 in SHIP$^{-/-}$ NK cells as compared to WT. The effect of the SHP1 over-recruitment was reversed by inhibiting SHP1 enzymatic activity using either a broad acting tyrosine phosphatase inhibitor (NaOV) or a more selective SHP inhibitor (NSC119910). These results have led to the hypothesis that SHIP-deficiency leads not only to 2B4 receptor dominance, but 2B4L bias, as well as altered inhibitory signaling within the SHIP$^{-/-}$ NK cell. A model has been developed incorporating the key differences that exist within 2B4 signaling in the SHIP$^{-/-}$ and WT environment (FIG. 6).

Given that SHIP is a key inhibitor of the PI3K pathway, initially it was considered the possible over-recruitment of the PI3K subunits, p110 and p85 to 2B4, might be responsible for the qualitative change in 2B4 function in SHIP-deficient NK cells. Given that the inhibition of SHP1 was able to restore killing in SHIP$^{-/-}$ NK cells to WT levels it stands to reason that PI3K does not play a major role in rendering SHIP$^{-/-}$ NK cells hypo-responsive. PI3K could still play a subtle and indirect role in 2B4 receptor dominance. Both short and long isoforms of 2B4 are present in a WT NK cell, as well as possible activating and inhibitory signaling molecules (FIG. 6A). The signal that is delivered, either activation or inhibition, depends upon the ligand present and the context of the signal. However, the 2B4 signaling in a SHIP−/− NK cell shows a lack of SHIP expression and bias towards the 2B4L isoform (FIG. 6B). These 2 factors lead to a profound increase in SHP1 recruitment and therefore tip the balance towards constitutive inhibitory signaling. The lack of SHIP may also allow unopposed PI3K activity at 2B4 that may in turn promote increased 2B4 expression. As is detailed in FIG. 6, in the absence of SHIP, PI3K activity may not need to be increased, but rather its' unopposed activity could potentially alter 2B4 expression and contribute to receptor dominance. Previous studies have identified AP-1 binding sites in the promoter of 2B4. PI3K can trigger nuclear translocation of AP-1 via activation of PKC-δ, and thus unopposed PI3K activity at 2B4 could potentially increase 2B4 expression and/or bias isoform usage towards 2B4L.

2B4 has proven to have a somewhat complex role in NK biology with in vitro and in vivo experiments indicating both activating and inhibitory roles in NK function. This disparity has been attributed, to some extent, to the various signaling adaptors that can potentially associate with the ITSM of 2B4. Both SHP1 and SHP2 have been shown to be recruited to 2B4 in certain contexts and are also key regulators of inhibitory signaling for MHC-I receptors on NK cells. This study identified a ~10 to 16 fold increase in SHP1 recruitment to 2B4 in the SHIP$^{-/-}$ NK cell. This is a key finding given that we have previously shown that the surface expression of 2B4 is increased only ~2 fold in the SHIP$^{-/-}$ NK cell compared to the WT NK cell. There is clearly a qualitative change in the 2B4 receptor complexes such that a much larger proportion of 2B4 molecules associate with SHP1 in the absence of SHIP expression. 2B4 has up to 4 tyrosine residues in its cytoplasmic tail that can be phosphorylated and recruit downstream signaling molecules. Both SHIP and SHP1 have SH2 domains that can bind overlapping phosphotyrosines in 2B4. Thus, in the SHIP-deficient NK cell there is likely greater access to 2B4 by SHP1. This dramatic increase of SHP1 at 2B4 receptor complexes could alter the balance of signaling in the SHIP-deficient NK cell. Importantly 2B4 has been shown to be recruited to the NK synapse. Therefore, the increased presence of SHP1 at the NK synapse in SHIP$^{-/-}$ NK cells is likely to terminate activating signals before they propagate to more distal effectors required for NK function. It is also important to note that the over-recruitment of SHP1 in LAK cells is likely to be occurring in the presence of 2B4 CD48 receptor ligand interactions. It has been previously shown that NK cells ubiquitously express CD48, thereby allowing a 2B4 CD48 interaction to occur in LAK cultures. In fact it has been shown that the 2B4 CD48 interaction is important in inhibiting NK fratricide, indicating that this interaction is not only theoretically possible but is actually a key interaction within NK cells. Therefore when 2B4 is examined in LAK cells it is probable that the receptor is examined in an engaged state.

This demonstration that killing of tumor targets by SHIP-deficient NK cells can exceed that of WT NK cells establishes an approach to enhance NK killing of tumors in vivo, and in the absence of NK activating ligand expression. The inventors show that dual or tandem inhibition of SHIP1 and SHP1 might be used to temporarily increase NK clearance of tumor cells. An illustrative embodiment includes the inhibition of SHIP to create an NK compartment that is overly dependent on one or limited number of inhibitory receptors that limit tumor killing. This is followed by treatment with a SHP1 inhibitor to unleash the killing capacity of the NK compartment cells against tumor cells. The examples disclosed herein used SHIP$^{-/-}$ NK cells and chemical inhibition of SHP1 activity. It is possible, however, to reversibly inhibit SHIP and SHP1 using RNA interference and/or chemical inhibitors. Due to the potential for autoreactivity, and the known deleterious consequences of prolonged SHIP deficiency, such an approach should only be done reversibly and not for sustained periods.

The finding that NSC119910 can also facilitate killing of tumor targets by SHIP-competent NK cells, even when the tumor target lacks an activating ligand, shows that administration of NSC119910 alone may also be used to chemically enhance NK activity against malignancies, and potentially intracellular pathogens.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of modulating activation of natural killer cells, comprising the step of contacting a population of natural killer cells with a therapeutically effective amount of NSC119910.

2. The method of claim 1, further comprising the step of:
contacting said population of natural killer cells with a therapeutically effective amount of a SHIP inhibitor.

* * * * *